(12) United States Patent
Speed et al.

(10) Patent No.: US 9,770,316 B1
(45) Date of Patent: Sep. 26, 2017

(54) DENTAL MAINTENANCE KIT FOR ANIMALS

(76) Inventors: Terri Lynn Speed, Elk Grove, CA (US); Marvin Ernest Speed, II, Elk Grove, CA (US)

( * ) Notice: Subject to any disclaimer, the term of this patent is extended or adjusted under 35 U.S.C. 154(b) by 503 days.

(21) Appl. No.: 13/385,517

(22) Filed: Feb. 22, 2012

Related U.S. Application Data

(63) Continuation-in-part of application No. 12/931,203, filed on Jan. 25, 2011.

(51) Int. Cl.
*A61B 19/02* (2006.01)
*A61C 19/02* (2006.01)
*A61C 3/00* (2006.01)

(52) U.S. Cl.
CPC .............. *A61C 19/02* (2013.01); *A61C 3/00* (2013.01)

(58) Field of Classification Search
CPC .... A61C 3/00; A61C 3/02; A61C 3/12; A61C 7/00; A61C 19/02; A46B 17/08
USPC .............. 206/63.5, 223, 229, 570, 572, 581; 132/309; 433/31, 46, 143, 146
See application file for complete search history.

(56) References Cited

U.S. PATENT DOCUMENTS

| | | | | |
|---|---|---|---|---|
| 1,684,417 A * | 9/1928 | Silberman | ...................... | 206/229 |
| 1,707,952 A * | 4/1929 | Schneider | ...................... | 433/144 |
| 3,366,230 A * | 1/1968 | Loran | ........................... | 206/63.5 |
| 3,921,649 A * | 11/1975 | Milbrath | ........................ | 132/308 |
| 4,022,879 A * | 5/1977 | Dietrich | .......................... | 424/49 |
| 4,293,074 A * | 10/1981 | Dunsky | ........................... | 206/572 |
| 4,828,113 A * | 5/1989 | Friedland et al. | ............ | 206/570 |
| 5,090,907 A * | 2/1992 | Hewitt et al. | ................. | 433/144 |
| 5,217,372 A * | 6/1993 | Truocchio | ..................... | 433/215 |
| 5,626,227 A * | 5/1997 | Wagner et al. | ............... | 206/369 |
| 6,102,051 A * | 8/2000 | Neves | ........................... | 132/321 |
| 6,109,918 A * | 8/2000 | Hammond et al. | ........... | 433/141 |
| 6,199,457 B1* | 3/2001 | Hoff et al. | ................. | 81/177.85 |
| 6,206,192 B1* | 3/2001 | Winstead et al. | ............. | 206/572 |
| 6,247,477 B1* | 6/2001 | Wagner | .......................... | 132/309 |
| 6,322,362 B1* | 11/2001 | Holms | .......................... | 433/143 |
| 6,729,877 B2* | 5/2004 | Rahman | ......................... | 433/141 |
| 6,905,335 B2* | 6/2005 | Fischer | ........................... | 433/77 |
| 2004/0038176 A1* | 2/2004 | Hallows | ........................ | 433/141 |
| 2004/0187888 A1* | 9/2004 | Vandyke | ....................... | 132/309 |
| 2006/0027246 A1* | 2/2006 | Wilkinson | ..................... | 132/309 |
| 2006/0110701 A1* | 5/2006 | Cwik | ................................ | 433/31 |
| 2008/0227051 A1* | 9/2008 | Szwajkowski et al. | ......... | 433/24 |

* cited by examiner

*Primary Examiner* — Anthony Stashick
*Assistant Examiner* — Ernesto Grano
(74) *Attorney, Agent, or Firm* — Risto A Rinne, Jr.

(57) ABSTRACT

A set of tools for removal of stains and debris from an animal's teeth includes an intraoral tool equipped with detachably-attachable sickle blade and scaler blade. Each blade includes a recessed area that is used to accept a desired quantity of meat-flavored toothpaste or other food therein. The toothpaste helps distract the animal from the teeth cleaning process. A preferred material for the intraoral tool is non-metallic and the blades are preferably stainless steel. A means to secure the blades to the intraoral tool is provided. A non-metallic coating is preferably applied to a base of each blade. A guide is included that provides written instructions for the use of the intraoral tool and various component parts.

13 Claims, 9 Drawing Sheets

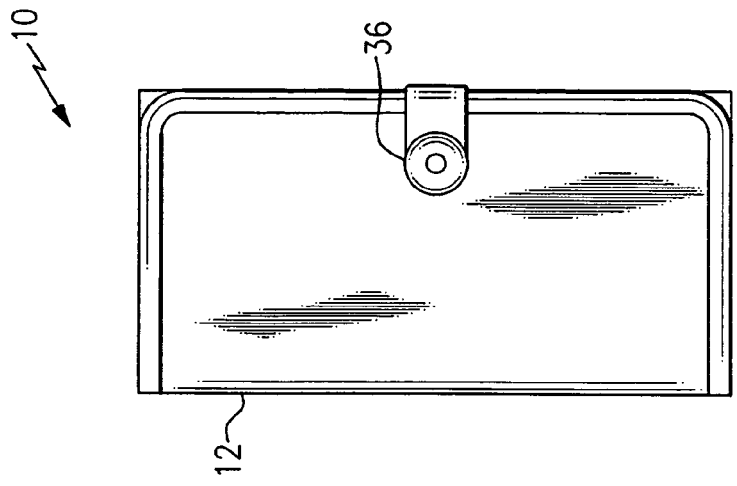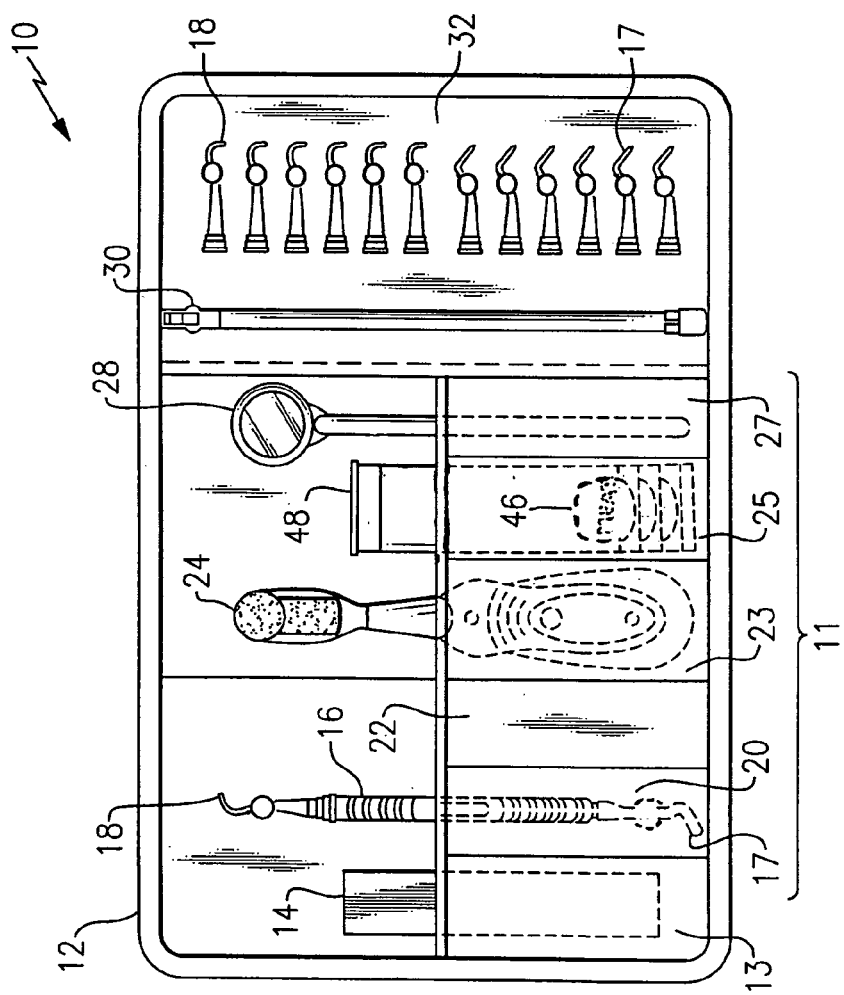

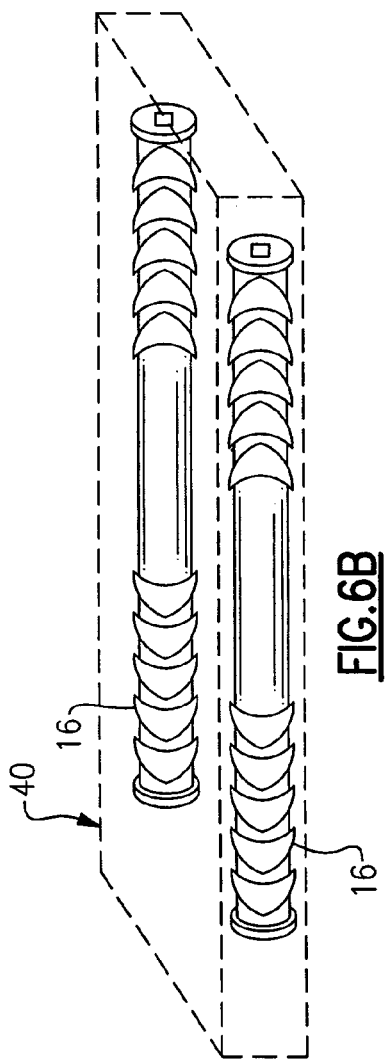
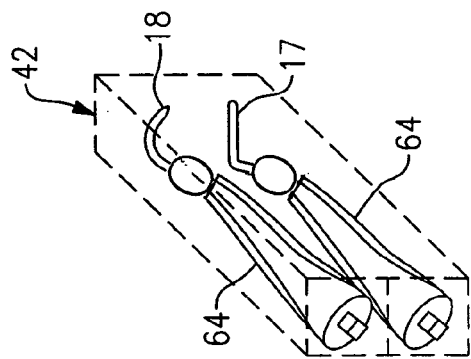
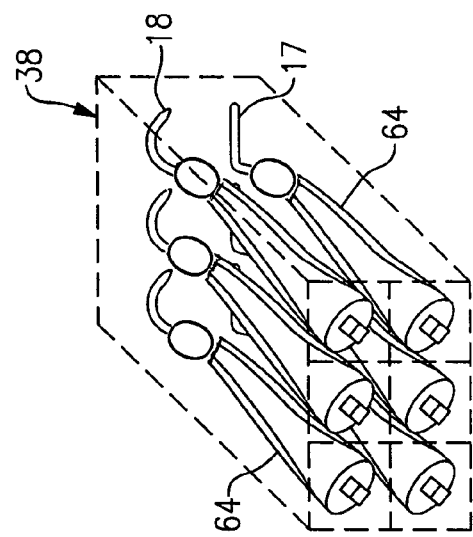
FIG. 6B
FIG. 6C
FIG. 6A

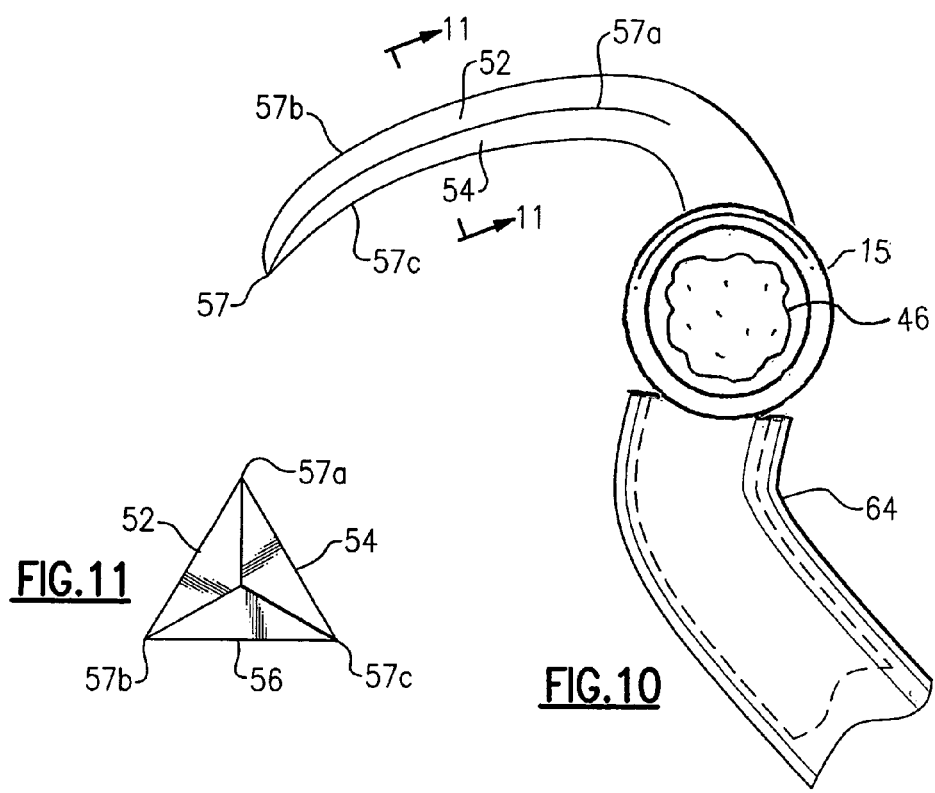
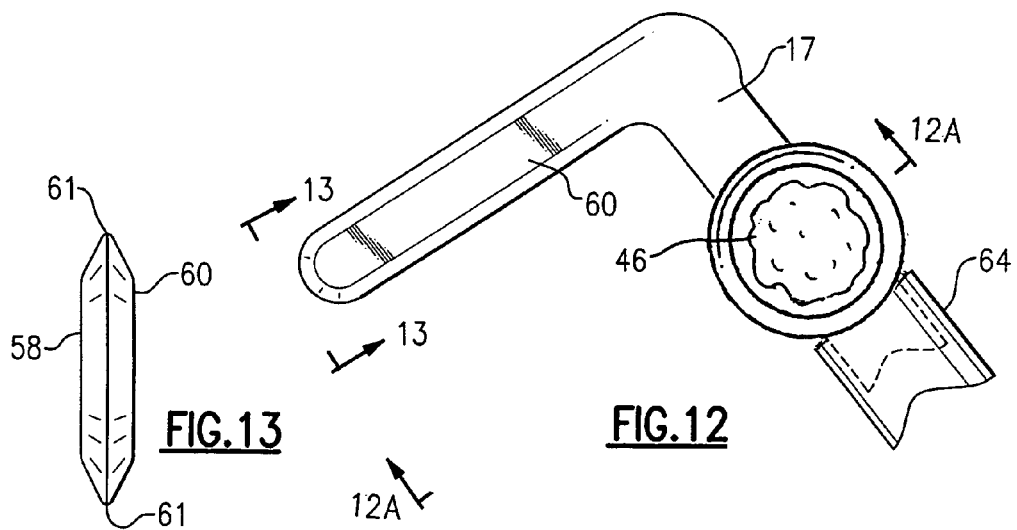

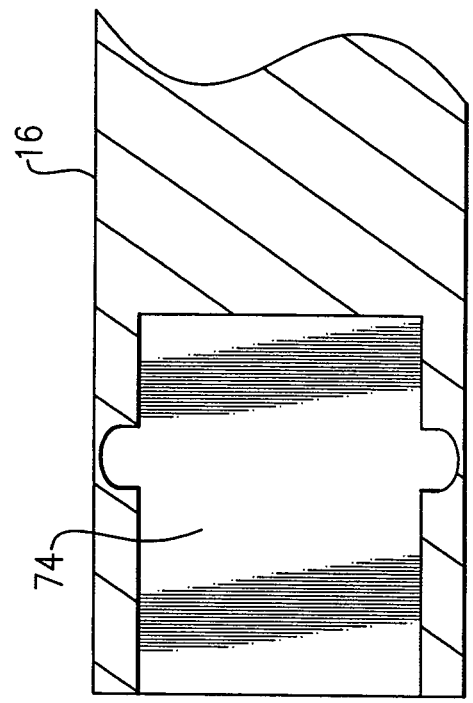
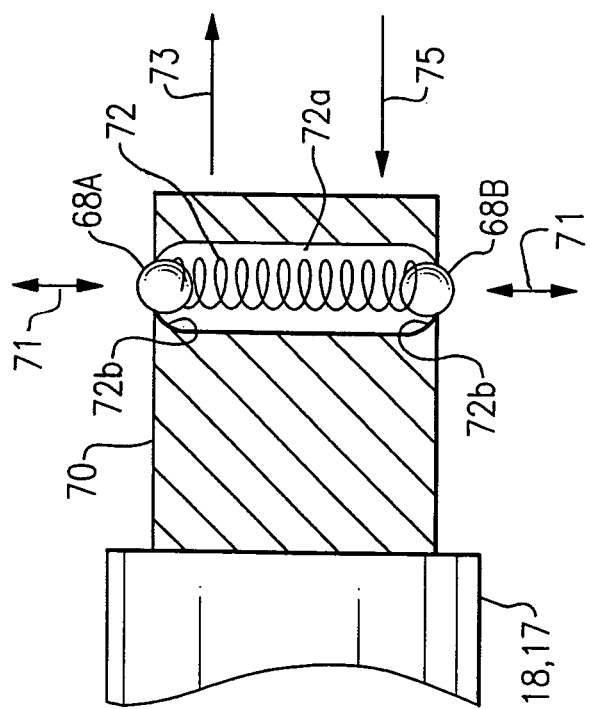
FIG. 16B
FIG. 16A

DENTAL MAINTENANCE KIT FOR ANIMALS

This application is a continuation-in-part of prior patent application Ser. No. 12/931,203 that was filed by the same inventors on Jan. 25, 2011, and claims the benefit of priority, thereof. The content of patent application Ser. No. 12/931,203 is included herein, by reference.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention, in general, relates to dentistry and, more particularly, to dental prophylaxis for animals.

For humans, the American Dental Association recommends that individuals have a dental exam and cleaning at least once per year. The regular cleaning and removal of plaque is known to reduce the possibility of developing gum disease. By routine brushing and flossing, humans are able to offset the potential for the development of gum disease and other types of dental maladies.

Unfortunately, animals owned as pets (i.e., cats and dogs) are not able to routinely clean their teeth on their own. The animal's teeth may begin to discolor and their gums may become swollen and inflamed if proper cleaning is not administered. In addition, an unhealthy mouth can lead to the animal having odorous breath. The pet owner may then schedule an appointment with a veterinarian to perform a thorough teeth cleaning.

However, one of the problems relating to scheduling an appointment with a veterinarian is that some pet owners are unable to schedule the appointments for various reasons such as time, availability, and financial limitations. The cost for performing regular teeth cleanings on the animal may not be affordable for the pet owner. As such, the pet owner may then forego the necessary teeth cleaning for the animal, thus placing the animal at risk for future dental problems. As the animal get older, lack of proper teeth cleaning may escalate into larger dental problems that are even more costly to attend to.

If the pet owner does take the animal to the veterinarian for teeth cleaning, the animal may not tolerate the teeth cleaning procedure. The animal may dislike the process and not tolerate the cleaning long enough for a complete cleaning of all their teeth. The veterinarian may then resort to securing the animal in place while the teeth cleaning process is accomplished. However, this may provide additional stress on the animal and further increase cost to the pet owner.

If the animal is still unable to allow the teeth cleaning process to be completed, use of an anesthetic may be required to sedate the animal. If the anesthetic is used, risk to the animal's health may arise. The anesthetic may increase the risk of kidney damage occurring. In addition, if the anesthetic is not properly administered, or if an allergic reaction occurs, death of the animal may even occur.

There remains a need to remove plaque, tartar, stains and even food that has been lodged in between the animal's teeth. Also, there remains a need for teeth cleaning for aesthetic reasons. The pet owner may desire that their pet's teeth look nice and that their breath should emit less odor.

Currently available animal treats being sold are designed to help clean the animal's teeth while they are eaten. If the treats are eaten too quickly they are ineffective in removing plaque, dental stains, and food debris.

Because of most animal's unwillingness to tolerate touching their mouth, let alone trying to clean their teeth, most pet owners are utterly unable to do so. Even a simple brushing of the teeth is beyond the capability of most pet owners. Still, there remains a need for periodic lower cost effective cleaning of an animals teeth that can be readily accomplished by a pet owner.

If a pet owner were to obtain a dental cleaning tool, such as a sickle blade or a scaler blade, and attempt to use it to clean their pet's teeth, there is risk of applying excessive force and damaging the teeth.

Accordingly, there exists today a need for a dental maintenance kit that helps to ameliorate the above-mentioned problems and difficulties as well as ameliorate those additional problems and difficulties as may be recited in the "OBJECTS AND SUMMARY OF THE INVENTION" or discussed elsewhere in the specification or which may otherwise exist or occur and that are not specifically mentioned herein.

As various embodiments of the instant invention help provide a more elegant solution to the various problems and difficulties as mentioned herein, or which may otherwise exist or occur and are not specifically mentioned herein, and by a showing that a similar benefit is not available by mere reliance upon the teachings of relevant prior art, the instant invention attests to its novelty. Therefore, by helping to provide a more elegant solution to various needs, some of which may be long-standing in nature, the instant invention further attests that the elements thereof, in combination as claimed, cannot be obvious in light of the teachings of the prior art to a person of ordinary skill and creativity.

Clearly, a dental maintenance kit for animals would be useful and desirable.

2. Description of Prior Art

Dental maintenance for animals is in general known. For example, toothbrushes specifically designed for animals and tartar cleaning treats are known. These items are designed to address superficial and cosmetic teeth cleaning. These items do not include a specific selection of tools and materials that enable a pet owner to perform a more comprehensive cleaning or remove debris or particles from between teeth which may cause discomfort or inflammation of the gums.

While the structural arrangements of the above described devices may, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a dental maintenance kit for animals that permits pet owners to perform dental prophylaxis on their pets (i.e., animals).

It is also an important object of the invention to provide a dental maintenance kit for animals that helps make a teeth cleaning process less objectionable to a pet.

Another object of the invention is to provide a dental maintenance kit for animals that permits a teeth cleaning process to be more enjoyable to a pet.

Still another object of the invention is to provide a dental maintenance kit for animals that increases an amount of time that a pet will allow for the cleaning of their teeth.

Still yet another object of the invention is to provide a dental maintenance kit for animals that masks a teeth cleaning process so that a pet is unaware that their teeth are being cleaned.

Yet another important object of the invention is to provide a dental maintenance kit for animals that conditions a pet to want to have their teeth cleaned.

A first continuing object of the invention is to provide a dental maintenance kit for animals includes an intraoral tool that can be used to remove debris that is embedded between teeth.

A second continuing object of the invention is to provide a dental maintenance kit for animals that includes an intraoral tool that includes removable and replaceable blades.

A third continuing object of the invention is to provide a dental maintenance kit for animals that includes an intraoral tool that includes blades with a release feature that allows the blades to detach from the intraoral tool if an excessive force is applied during use.

A fourth continuing object of the invention is to provide a dental maintenance kit for animals that includes an intraoral tool with a sickle blade attached at a first end thereof and a scaler blade attached at an opposite second end thereof.

A fifth continuing object of the invention is to provide a dental maintenance kit for animals that includes a recessed area located on a base portion of a sickle or a scaler blade.

A sixth continuing object of the invention is to provide a dental maintenance kit for animals that includes a recessed area located on a base portion of a sickle or a scaler blade for placement of a quantity of a flavored toothpaste.

A seventh continuing object of the invention is to provide a dental maintenance kit for animals that includes a meat-flavored toothpaste that is safe for consumption and ingestion by a pet.

An eighth continuing object of the invention is to provide a dental maintenance kit for animals that includes a recessed area located on a base portion of a sickle or a scaler blade for placement of a quantity of a soft pet food.

A ninth continuing object of the invention is to provide a dental maintenance kit for animals that includes a plastic coating at a lower portion of a sickle or a scaler blade that only exposes a tip and a recessed area of either blade to prevent injury to a pet.

A tenth continuing object of the invention is to provide a dental maintenance kit for animals that includes a detachably-attachable sickle or a scaler blade that has a protrusion that fits within a recess provided in a plastic handle of an intraoral tool to secure the blade to the intraoral tool.

An eleventh continuing object of the invention is to provide a dental maintenance kit for animals that includes an intraoral tool and at least one sickle blade and at least one scaler blade for attachment thereto.

A twelfth continuing object of the invention is to provide a dental maintenance kit for animals that includes a detachably-attachable sickle or a scaler blade that has a mounting mechanism which acts as a safety release if an intraoral tool is subjected to excess prying or, pulling pressure.

A thirteenth continuing object of the invention is to provide a dental maintenance kit for animals that includes a toothbrush which may be specifically designed for use with animals.

A fourteenth continuing object of the invention is to provide a dental maintenance kit for animals that optionally includes a standard dental mirror.

A fifteenth continuing object of the invention is to provide a dental maintenance kit for animals that includes printed instructions for proper use of items included within the kit.

A sixteenth continuing object of the invention is to provide a dental maintenance kit for animals that includes at least one tube or container of a meat-flavored toothpaste.

A seventeenth continuing object of the invention is to provide a dental maintenance kit for animals that is designed for easy and safe usage on a pet.

An eighteenth continuing object of the invention is to provide a dental maintenance kit for animals that includes specialized tools that allow for comprehensive plaque and debris removal.

A nineteenth continuing object of the invention is to provide a dental maintenance kit for animals that includes an intraoral tool with a plurality of blades which can be replaced when they are damaged or become dull or, if desired, when a different type of blade is preferred.

A twentieth continuing object of the invention is to provide a dental maintenance kit for animals that provides an affordable solution for animal dental care instead of a veterinarian appointment.

A twenty-first continuing object of the invention is to provide a dental maintenance kit for animals that includes a dental prophylaxis tool for performance of dental intraoral maintenance that is inexpensive.

A twenty-second continuing object of the invention is to provide a dental maintenance kit for animals that includes a securable foldable pouch for storage of component parts within the kit and allows the kit to be easily portable.

A twenty-third continuing object of the invention is to provide a dental maintenance kit for animals that can extend the time between veterinary visits by allowing a pet owner to clean the teeth of their pet.

Briefly, a dental maintenance kit for animals that is constructed in accordance with the principles of the present invention preferably has a pouch that is foldable and subdivided into individual pockets. The individual pockets are used to house specific tools and accessories designed for dental maintenance on an animal. A button, a snap or other desired means to secure the pouch in a closed position may be included on the pouch. The pouch is preferably foldable at a mid-point and the button or the snap is used to secure the pouch from unintentional opening. At least one intraoral tool is included in the dental maintenance kit for animals. If desired, additional intraoral tools may be purchased at additional cost. The intraoral tool may be used on dogs or cats in particular, however the intraoral tool may also be used on less common types of animals (i.e., pets). The intraoral tool includes a longitudinal body preferably made of a hard resin such as plastic, however any preferred material may be used. The body of the intraoral tool functions as a handle during use. The body of the intraoral tool includes means at a first end and an opposite second end thereof for insertion and removal of a replaceable dental cleaning blade at each end. A sickle blade is attached to the first end (or second end) of the intraoral tool. A scaler blade is attached to the remaining opposite end of the intraoral tool. The sickle and the scaler blade are common tools within the dental arts used for cleaning of plaque and tarter from teeth. The sickle blade is curved in design and includes a pointed tip. The scaler blade includes a linear design and a more rounded tip. At least one sickle blade and at least one scaler blade are included in the dental maintenance kit for animals. If desired, additional sickle or scaler blades may be included with the kit or may be purchased separately at additional cost. A pocket with a zipper closure is preferably provided within an interior of the pouch to contain one or more spare blades for use on the intraoral tool. The sickle and the scaler blades each include a recessed area located on a base member of the blade. The recessed area includes a shape that is similar to that of a small spoon. The recessed area is used to apply a desired quantity of a meat-flavored toothpaste. A tube (or tubes) of the meat-flavored toothpaste is preferably included in the dental maintenance kit for animals. The toothpaste is meant to be ingested and is safe for swallowing. The toothpaste aids in the cleaning process of the animal's teeth and also distract the animal from the teeth cleaning process. Alternately, a quantity of a soft pet food (i.e., canned pet food) may be applied to the recessed area. A pet owner (or other individual) inserts the sickle and the scaler blade on the first and the second ends of the intraoral tool. The pet owner then places the desired quantity of the toothpaste or pet food on the recessed area of either the sickle or the scaler blade, depending on which blade is to be used first. As the pet owner begins cleaning the animal's teeth, the animal is able to lick the toothpaste or food from the recessed area on the blade. Since the pet is focused on the meat-flavored toothpaste or the pet food, the animal is considerably less aware of the teeth cleaning process that is occurring. The animal will begin to associate the teeth cleaning process with receiving a special treat, thus conditioning the animal to respond favorably to the teeth cleaning process. A toothbrush, either battery powered or manually operated, is included in the dental maintenance kit for animals. The meat-flavored toothpaste may also be used on the toothbrush to clean the animal's teeth. A standard dental mirror may optionally be included in the dental maintenance kit to assist the pet owner in seeing inside the animal's mouth. An instructional guide is provided to teach an unskilled pet owner how to safely use the intraoral tool and effectively clean the teeth of their pet.

BRIEF DESCRIPTION OF THE DRAWINGS

FIG. 1A is a top view of a dental maintenance kit for animals with a storage pouch shown in an open orientation with a plurality of components therein.

FIG. 1B is a side view of the dental maintenance kit for animals of FIG. 1A that shows the pouch in a closed orientation.

FIG. 6A is a view in perspective of a first packaging option for a purchase of additional or replacement blades consisting of three sickle blades and three scaler blades.

FIG. 6B is a view in perspective of a second packaging option for the purchase of additional or replacement intraoral tools consisting of two intraoral tools.

FIG. 6C is a view in perspective of a third packaging option for the purchase of an additional or replacement sickle blade and scaler blade.

FIG. 9 is a top view of a standard type dental mirror for inclusion with the dental maintenance kit for animals of FIG. 1A.

FIG. 10 is a partial side view of the sickle blade showing detail of the recessed area during use.

FIG. 11 is a cross sectional view taken along line 11-11 in FIG. 10 of the sickle blade.

FIG. 12 is a partial side view of the scaler blade showing the recessed area.

FIG. 13 is a cross sectional view taken along the line 13-13 in FIG. 12 of the scaler blade.

FIG. 16A is a cross sectional view taken along line 16A-16A in FIG. 14 of a locking mechanism incorporated into a protrusion located at the base of each sickle (or scaler) blade.

FIG. 16B is a cross sectional view of a receiver taken along line 163-16B in FIG. 15 of the intraoral tool.

DETAILED DESCRIPTION OF THE INVENTION

Figure 2:
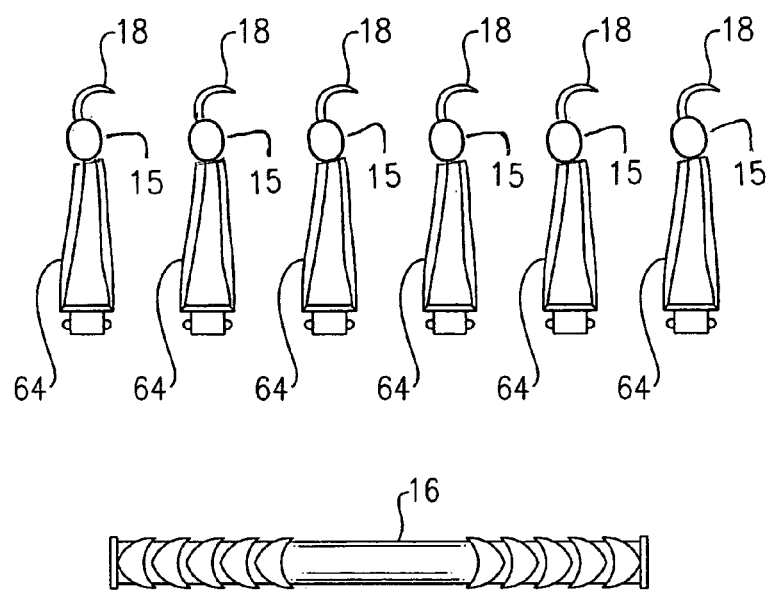
FIG. 2 is a side view of an intraoral tool of the dental maintenance kit for animals of FIG. 1A and a plurality of sickle blades with a recessed area.

Referring on occasion to all of the FIGURE drawings and now, in particular to FIG. 1A, is shown a dental maintenance kit for animals, identified in general, by the reference numeral 10.

The reader will notice that reference is occasionally made throughout the DETAILED DESCRIPTION OF THE INVENTION suggesting that the reader refer to a particular drawing FIGURE. The suggestion is at times made when the introduction of a new element requires the reader to refer to a different drawing FIGURE than the one currently being viewed and also when the timely viewing of another drawing FIGURE is believed to significantly improve ease of reading or enhance understanding. To promote rapid understanding of the instant invention the reader is encouraged to periodically refer to and review each of the drawing FIGURES for possible cross-referencing of component parts and for other potentially useful information.

Certain examples are shown in the above-identified FIGURES and are described in greater detail below. In describing these examples, like or identical reference numerals may be used to identify common or similar elements.

The dental maintenance kit for animals 10 is intended for the performance of routine dental care on an animal (i.e., a pet). When done by a pet owner, the dental maintenance kit for animals 10 can extend the time between visits to a veterinarian. The animal is most likely to be a dog or a cat (not shown), but the dental maintenance kit for animals 10 may be used on other types of animals.

The dental maintenance kit for animals 10 is used to provide normal and routine dental cleaning and examination typically offered by a veterinarian. The dental maintenance kit for animals 10 may also be used in between veterinarian dental examinations or regular dental hygiene (prophylaxis) appointments.

The dental maintenance kit for animals 10 includes a pouch 12. The pouch 12 may be made of any desired material. The pouch 12 includes a plurality of pockets, identified by bracket 11, for the purpose of organizing and storage of preferred component parts that consist of the dental maintenance kit for animals 10. The specific component parts contained within the pouch 12 are described in greater detail, hereinafter. The arrangement of the plurality of pockets 11 can vary as desired, providing that each of the plurality of pockets 11 is of sufficient size and shape to accommodate the specific component part, therein.

The plurality of pockets 11 includes a first pocket 13. The first pocket 13, as shown, is used for storage of a guide 14. The guide 14 provides instructions and guidelines for proper use of the dental maintenance kit for animals 10. The guide 14 will include instructions for proper use of all of the component parts within the kit 10 and, in particular, for use of an intraoral tool 16.

The guide 14 allows an unskilled pet owner (not shown) to safely and properly provide dental care and maintenance on their pet. The guide 14 may be provided in more than one language. It may also be available on the Internet.

An adjacent second pocket 20 is disposed to the right of the first pocket 13. The second pocket 20 is for storage of the intraoral tool 16. The second pocket 20 is sized to accept the preferred basic configuration of the intraoral tool 16 that includes a sickle blade 18 and a scaler blade 17 attached at the opposite ends of the intraoral tool 16. The sickle 18 and the scaler 17 blades will each be described in greater detail, hereinafter.

A third pocket 22, to the right of the second pocket 20, as shown, is a pocket without a specific component designated for storage therein. The pocket 22 may be used for storage of additional quantities of components as are described in greater detail, hereafter. If desired, the pocket 22 may be used to store any preferred item (not shown) that the pet owner may wish to include that is not part of the dental maintenance kit for animals 10.

A fourth pocket 23 is disposed to the right of the third pocket 22. The fourth pocket 23 is utilized for storage of a toothbrush 24. The toothbrush 24 is described in greater detail, hereinafter.

A fifth pocket 25 is disposed to the right of the fourth pocket 23. The fifth pocket 25 is utilized for the storage of a plastic storage container 48 (see FIG. 8). The storage container 48, as shown, contains three containers of a meat-flavored toothpaste 46. The meat-flavored toothpaste 46 will be described in greater detail, hereinafter.

A sixth pocket 27 is disposed to the right of the fifth pocket 25 for the storage of a standard type of dental mirror 28. The dental mirror 28 is optionally included in the dental maintenance kit for animals 10 and is described in greater detail, hereinafter.

A seventh pocket 32 is disposed to the right of the sixth pocket 27 for the storage of extra sickle blades 18 and extra scaler blades 17. The seventh pocket 32 preferably includes a zipper 30 to prevent loss of spare sickle blades 18 or spare scaler blades 17. Spare blades 17, 18 are included in the dental maintenance kit for animals 10 or may be purchased at a later time and placed within the seventh pocket 32.

Referring now to FIG. 1B, the storage pouch 12 is shown in a closed position. The pouch 12, while in the closed position, is folded and secured with a snap button 36. The snap button 36 is used to prevent unintentional opening of the pouch 12 that can lead to a loss of components stored within an interior of the pouch 12. Numerous other variations in the design of the pouch 12 are possible. If desired, VELCRO™ could be used to secure the pouch 12 in the closed position. A zipper closure (not shown) is also possible.

The dental maintenance kit for animals 10 is comprised of dental components and parts that have been selected to work in conjunction with each other to provide options for regular cleaning of the animal's teeth, and, when desired, a more comprehensive cleaning.

Referring to FIG. 2, a side view of a plurality of the sickle blades 18 and a side view of the intraoral tool 16 is shown. The sickle blades 18 are secured to the intraoral tool 16, utilizing a locking mechanism that is described in greater detail, hereinafter.

The sickle blades 18 are curved in design and are used to access in-between the animal's teeth and lightly scrape the teeth's surface below a gum line.

A recessed area 15 is provided at a base of the sickle blade 18. The recessed area 15 is formed as part of the sickle blade 18. The recessed area 15 includes an oval or circular overall shape. The recessed area 15 includes a concave interior curvature (see FIG. 12A) that is shaped similar to a small spoon or bowl. A small quantity of the meat-flavored toothpaste 46 is applied directly to the recessed area 15. Since the recessed area is shaped like a spoon, the meat-flavored toothpaste 46 is effectively contained within the recessed area 15. If desired, a small quantity of a soft pet food (i.e., canned food) may be used instead of the meat-flavored toothpaste 46.

Before the pet owner begins the teeth cleaning process on the animal, the meat-flavored toothpaste 46 is placed within the recessed area 15. While the pet owner is using the sickle blade 18 attached to the intraoral tool 16, the animal is able to enjoy the flavor of the meat-flavored toothpaste 46 from the recessed area 15.

Inclusion of the recessed area 15 provides an unexpected benefit. As the meat-flavored toothpaste 46 includes an appetizing flavor (i.e., chicken, beef, liver, fish, etc.) the animal thinks it is being fed or receiving a special treat. This will allow the pet owner to clean the animal's teeth for a longer period of time.

A second additional unexpected benefit is provided in that the animal will want to have their teeth cleaned. They will be conditioned to know that when their teeth are cleaned, a treat is available for them to enjoy. By offering the meat-flavored toothpaste 46 or other soft food, it will mask the teeth cleaning process and the animal will find the cleaning process to be less objectionable.

Figure 3:
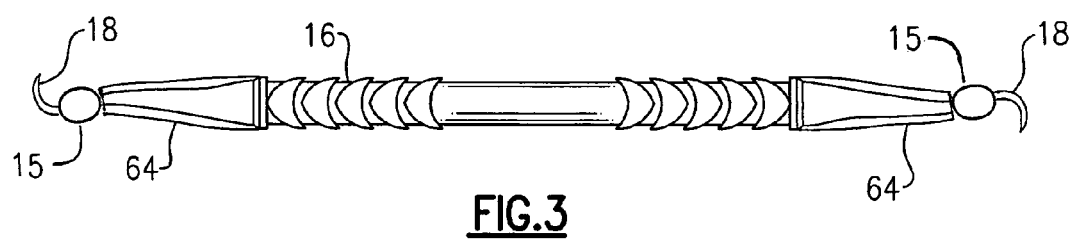
FIG. 3 is a side view of the intraoral tool of the dental maintenance kit for animals of FIG. 1A with a sickle blade attached at each end, thereof.

Referring to FIG. 3, the intraoral tool 16 is shown with the sickle blade 18 attached at each end of the intraoral tool 16. At a minimum one sickle blade 18 and one scaler blade 17 (see FIG. 4) are included in the dental maintenance kit for animals 10. The pet owner may attach the sickle blade 18 at a first end of the intraoral tool 16 and the scaler blade 17 at an opposite second end. If the additional blades 17, 18 are included with the dental maintenance kit for animals 10, or are purchased later, the pet owner may wish to attach the same types of blade 17, 18 at each end of the intraoral tool 16 for alternate use on the top and bottom teeth.

Figure 4:
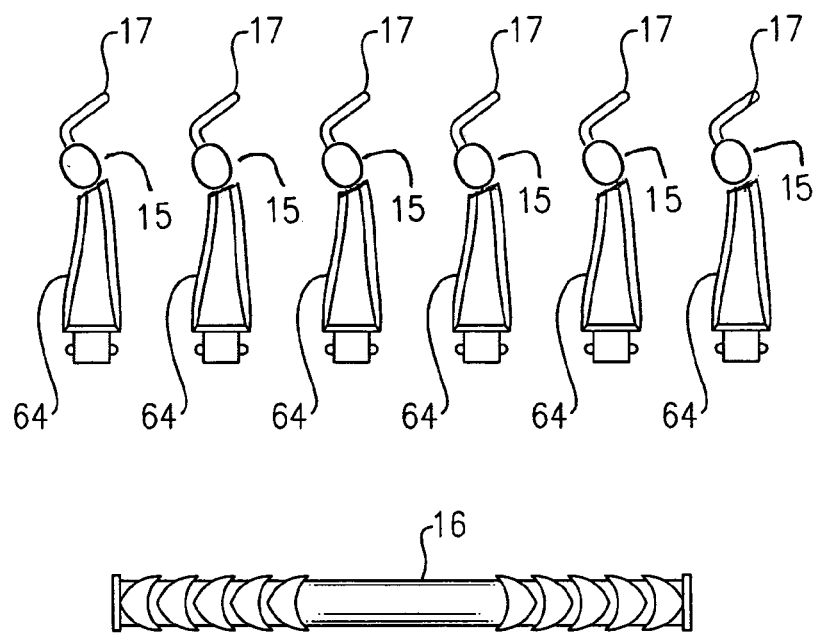
FIG. 4 is a side view of the intraoral tool of the dental maintenance kit for animals of FIG. 1A and a plurality of scaler blades with a recessed area.

Referring to FIG. 4, is shown a side view of a plurality of the scaler blades 17 and the intraoral tool 16. The scaler blades 17 are attached to the intraoral tool 16 using the locking mechanism, which was briefly mentioned previously. Each of the scaler blades 17 include the recessed area 15 for placement of the meat-flavored toothpaste 46 or other soft food.

The scaler blades 17 are linear in design and include a flat tip. The scaler blades 17 are used to scrape an exterior surface of the teeth to remove plaque, tartar and other build-up on the animal's teeth.

Figure 5:
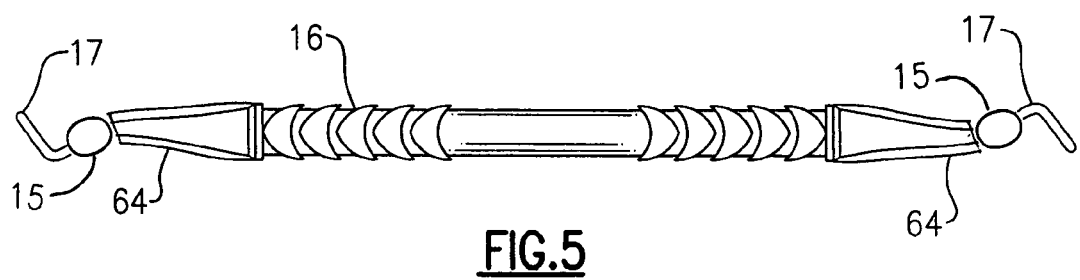
FIG. 5 is a side view of the intraoral tool of the dental maintenance kit for animals of FIG. 1A with a scaler blade attached at each end, thereof.

Referring to FIG. 5, a side view of the intraoral tool 16 is shown with the scaler blade 17 attached at each end of the intraoral tool 16. As mentioned earlier, a preferred intraoral tool 16 configuration is the sickle blade 18 attached at a first end and the scaler blade 17 attached at an opposite second end of the intraoral tool 16, as shown in FIG. 1A.

In general, the sickle blade 18 is often preferred for cleaning between teeth and the scaler blade 17 is often preferred for cleaning the teeth surfaces. Detailed safe cleaning instructions for using the sickle blade 18 and the scaler blade 17 are provided in the instruction guide 14.

Referring to FIG. 6A, a first packaging option is shown in dashed lines and is identified in general by reference numeral 38. The packaging option 38 includes three replacement sickle blades 18 and three replacement scaler blades 17. The packaged replacement blades 17, 18 are purchased at additional cost.

Referring to FIG. 6B, a second packaging option is shown in dashed lines and is identified in general by reference numeral 40. The second packaging 40 includes two replacement intraoral tools 16. The intraoral tool 16 is preferably made of plastic to minimize cost and weight. Use of plastic makes the dental maintenance kit for animals 10 less likely to be detected at airport security screening stations, should the kit 10 be taken during travel along with the animal.

Referring to FIG. 6C, a third packaging option is shown in dashed lines and is identified in general by reference numeral 42. The third packaging 42 includes a single sickle blade 18, and a single scaler blade 17.

The three packaging options 38, 40, and 42 are shown to illustrate possible ways offering replacement sickle blades 18, scaler blades 17 and the intraoral tool 16 for purchase should any of the above-mentioned items become worn or broken. It is to be understood that other quantity amounts of the sickle blades 18, the scaler blades 17 and the intraoral tools 16 may be included in any of the packaging options 38, 40, and 42.

Figure 7:
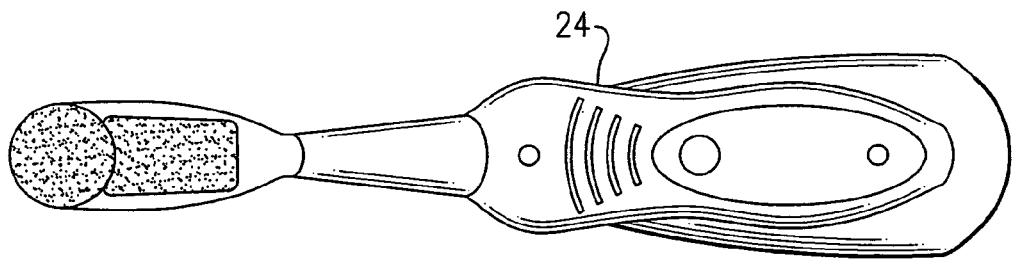
FIG. 7 is a top view of a toothbrush for inclusion with the dental maintenance kit for animals of FIG. 1A.

Referring to FIG. 7, is shown the toothbrush 24 that is included in the dental maintenance kit for animals 10. As shown, the toothbrush 24 is a battery-operated type with rotary bristles. The battery-operated toothbrush 24 may be helpful with certain types of animals or teeth cleaning needs. Alternately, the toothbrush 24 may also be a basic manual type of toothbrush or any other preferred design that is suitable for brushing the animal's teeth.

Figure 8:
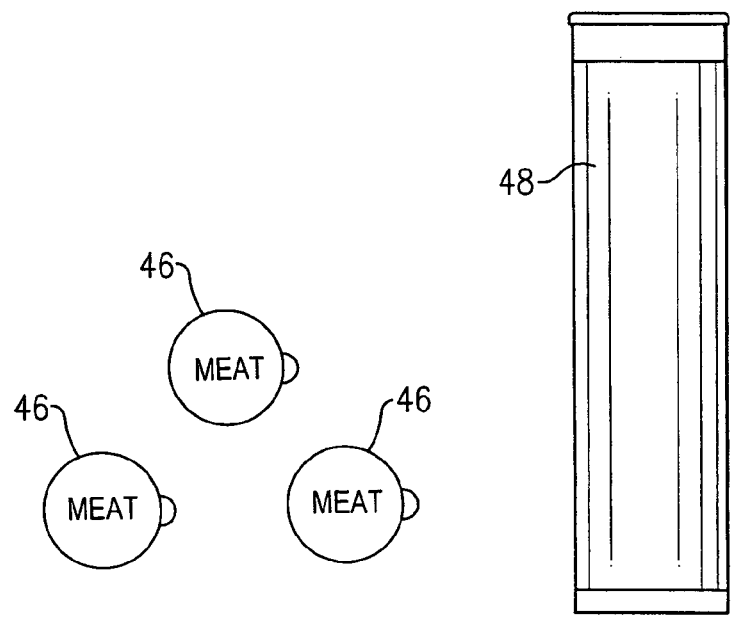
FIG. 8 is a top view of a plurality of meat-flavored toothpaste containers and a storage container for inclusion with the dental maintenance kit for animals of FIG. 1A.

Referring to FIG. 8, a plurality of the meat-flavored toothpaste containers 46 are shown removed from the plastic container 48. The meat-flavored toothpaste containers 46 may each be of a different flavor (i.e., chicken, beef, liver, fish, etc.) or all of the same flavor. Any number of flavors or containers may be included in the dental maintenance kit for animals 10.

In addition, the meat-flavored toothpaste 46 may also be provided in a tube (not shown) and the storage container 48 may be omitted. The dimensions of the storage case 48 allow for its insertion within the fifth pocket 25 of the pouch 12 of the dental maintenance kit for animals 10. If the meat-flavored toothpaste 46 is provided in the tube, the tube may also be sized to fit within the fifth pocket 25.

The meat-flavored toothpaste 46 is unlike regular toothpaste for humans. Warnings printed on toothpaste packaging advise humans not to swallow the toothpaste. Toothpaste for humans is not meant for consumption (i.e., swallowing). The meat-flavored toothpaste 46 is actually meant to be swallowed and consumed by the animal during the teeth cleaning process. In moderate quantities, the meat-flavored toothpaste 46 is safe for ingestion and therefore will not cause harm to the animal after it has been swallowed.

As mentioned previously, the meat-flavored toothpaste 46 provides an important and unexpected benefit. The meat-flavored toothpaste 46 placed on the recessed area 15 of either blade 17, 18 helps mask the teeth cleaning process so that the animal is less aware of the cleaning being performed. As such, the animal will allow the pet owner to complete a more thorough cleaning for a longer period of time. The animal will be conditioned to even want to have their teeth cleaned as they learn that there will be a benefit for them (i.e., eating the meat-flavored toothpaste 46).

As the pet owner is able to clean the animal's teeth on his or her own, it lessens the need for a teeth cleaning process performed by a veterinarian. Teeth cleaning performed by the veterinarian often involves use of anesthesia. The use of anesthesia incurs an element of risk to the animal's health. The use of the dental maintenance kit for animals 10 provides a safe and effective method for cleaning the animal's teeth.

The meat-flavored toothpaste 46 may also be used with the toothbrush 24 to brush the animal's teeth. It preferably includes a mild abrasive substance. The meat-flavored toothpaste 46 not only tastes good to the animal but also provides helpful benefits for oral health care.

Referring to FIG. 9, the dental mirror 28 included in the dental maintenance kit for animals 10 is shown. Inclusion of the dental mirror 28 within the kit 10 is optional.

A preferred reflective surface 50 of the dental mirror 28 is a zinc crystal compound used for standard types of dental mirrors although any preferred material may be used. The dental mirror 28 provides a safe means to observe a position and placement of the intraoral tool 16, including position of the sickle blade 18 and the scaler blade 17, in order to prevent injury to the animal.

The dental mirror 28 may also be used to view inside the animal's mouth to determine a location of where the plaque or food build-up may be located.

Referring to FIG. 10, a side view of the sickle blade 18 is shown with a detail view of a tapering of the sickle blade 18 to a point 57. The recessed area 15 is shown containing the meat-flavored toothpaste 46. As the sickle blade 18 is placed within the animal's mouth, the animal begins to lick the meat-flavored toothpaste 46 (or food) from the recessed area 15. Alternately, the animal's saliva helps dissolve the meat-flavored toothpaste 46 over the course of time, thereby keeping the animal happily engaged with the cleaning process.

The animal is distracted by the meat-flavored toothpaste 46 and is less objectionable to the pet owner using the sickle blade 18 on the intraoral tool 16 to clean their teeth.

The cross sectional view in FIG. 11 taken along the line 11-11 in FIG. 10 illustrates how the sickle blade 18 is comprised of three surfaces 52, 54, 56 that taper to the point 57. The point 57 also includes three edges 57a, 57b, 57c which are used to remove plaque and debris from the inter-proximal surfaces of the animal's teeth.

Referring to FIG. 12 a side view of the scaler blade 17 is shown illustrating how the tip of the scaler blade 17 is rounded in order to facilitate the removal of plaque and food-debris from the distal and the lingual surfaces of the animal's teeth. A quantity of the meat-flavored toothpaste 46 is also shown disposed in the recessed area 15.

Figure 12A:
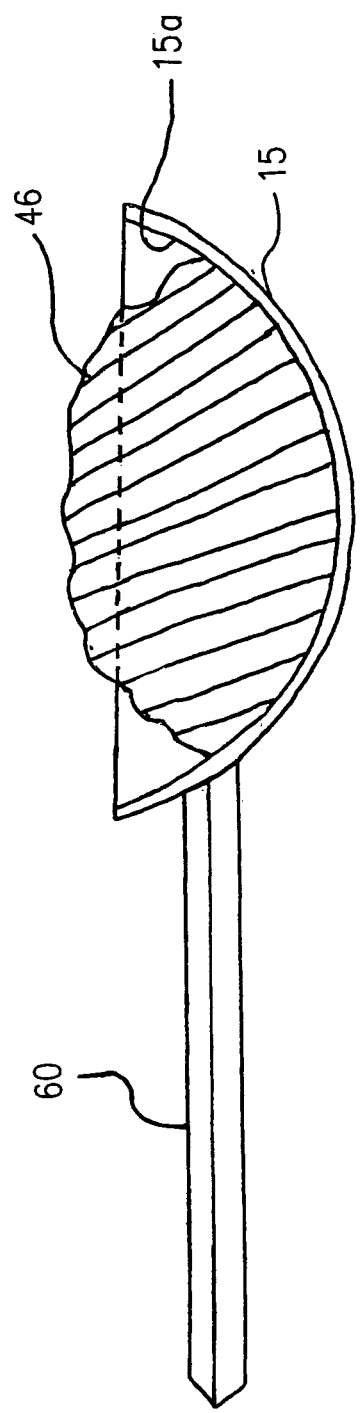
FIG. 12A is a cross sectional view taken along line 12A-12A in FIG. 12 of the recessed area.

Now referring to FIG. 12A, the recessed area 15 includes a concave interior portion 15a for placement of the meat-flavored toothpaste 46 or canned food. The meat-flavored toothpaste 46 adheres to the concave interior portion 15a. It is difficult for the animal to manipulate its tongue to contact and remove the meat-flavored toothpaste 46. This helps prolong the time that the meat-flavored toothpaste 46 remains on the recessed area 15 which, in turn, prolongs the time for cleaning. When necessary, the user (i.e., pet owner) removes the intraoral tool 16 from the animal's mouth and adds an additional quantity of the meat-flavored toothpaste 46 to continue the cleaning process.

Referring to FIG. 13, a cross sectional view taken along line 13-13 in FIG. 12 shows how a working end of the scaler blade 17 is comprised of two flat surfaces 58, 60 that taper on opposite ends to an edge 61. The edge 61 helps scrape plaque and food-debris off of the surfaces of the animal's teeth.

Figure 14:
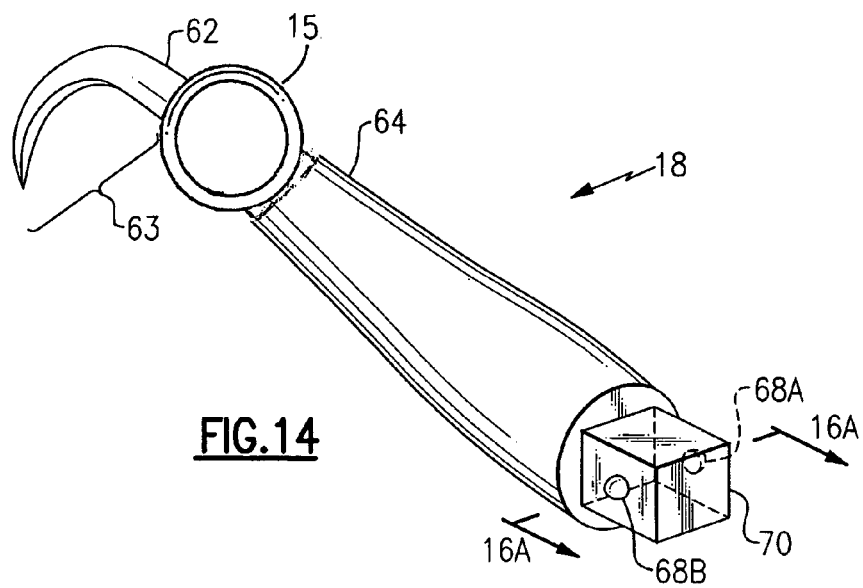
FIG. 14 is a view in perspective of the sickle blade prior to attachment to the intraoral tool.

Referring to FIG. 14, the sickle blade 18 is shown detached from the intraoral tool 16. The sickle blade 18 and the scaler blade 17 each attach to the intraoral tool 16 in the same unique way. Each sickle blade 18 and scaler blade 17 is preferably comprised of an active blade portion 62 that located above the recessed area 15. When the pet owner is using the active blade portion 62 to clean the animal's teeth, the animal is able to lick the meat-flavored toothpaste 46 (or the pet food) from the recessed area 15 or access the meat-flavored toothpaste 46 by their saliva dissolving it.

A base of each of the sickle and scaler blades 18, 17 preferably includes a plastic covering or coating 64. The plastic covering 64 is used to protect the base of the either blade 18, 17 from impacting any surface inside the animal's mouth. The plastic covering 64, is disposed over the base of the sickle blade 18 (and the scaler blade 17), which helps to prevent an unskilled pet owner from inadvertently cutting the animal's gums.

The plastic covering 64 terminates proximate the recessed area 15, leaving exposed a working surface, identified by bracket 63, of the active portion 62. The working surface 63 of the blade 17, 18 is the area primarily used for the teeth cleaning process.

The plastic covering 64 extends from the recessed area 15 of the sickle blade 18 (and the scaler blade 17) to an opposite lower end of the blade 17, 18. The lower end includes a square-shaped protrusion 70. The plastic covering 64 does not extend over the protrusion 70. The protrusion 70 is equipped with a pair of locking spheres 68A, 68B that are used to secure the sickle blade 18 (or the scaler blade 17) to the intraoral tool 16. (see also FIGS. 16A and 16B). The locking spheres 68A, 68B are described in greater detail, hereinafter.

Figure 15:
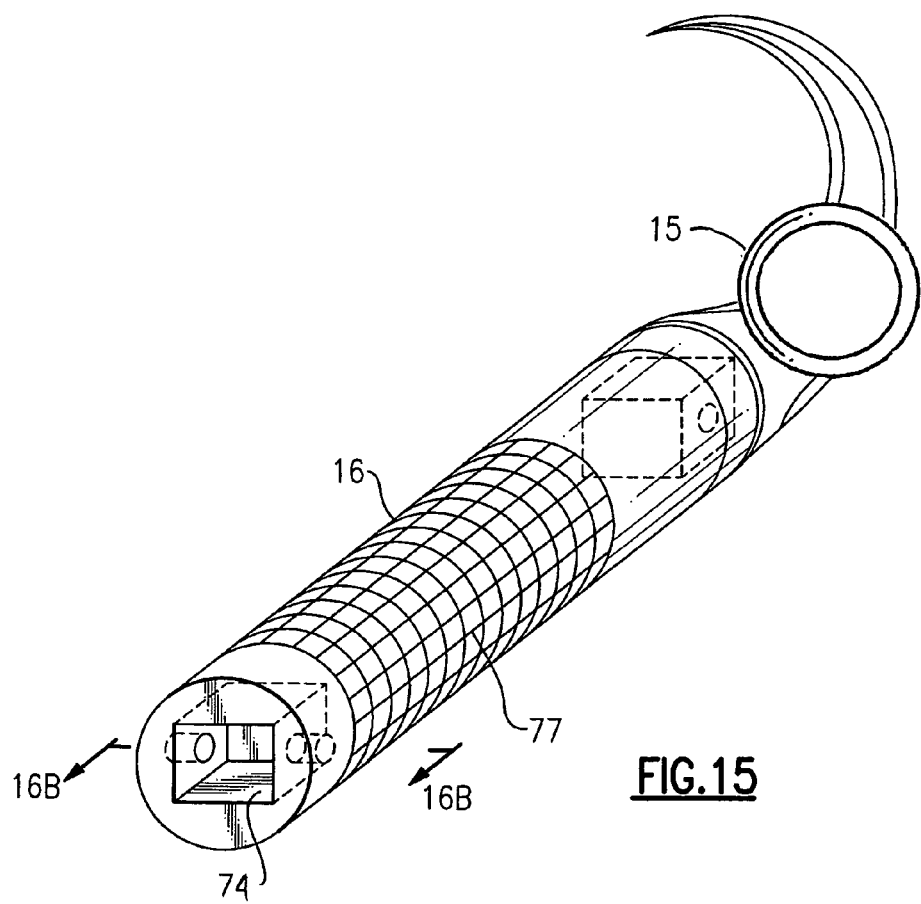
FIG. 15 is a view in perspective of the intraoral tool of the dental maintenance kit for animals of FIG. 1A with the scaler blade attached to a first end of the intraoral tool with a second end of the intraoral tool open for clarity.

Referring to FIG. 15, the intraoral tool 16 is shown with the sickle blade 18 attached at the first end and the scaler blade 17 removed from the second end for clarity.

A preferred material, as previously mentioned, for the intraoral tool 16 is plastic. The intraoral tool 16 preferably includes a knurled surface 77 to provide a secure grip during installation and removal of sickle blades 18 or scaler blades 17 and during use of the intraoral tool 16 while cleaning the animal's teeth.

Referring to FIG. 16A, a cross-sectional view taken along line 16A-16A in FIG. 14, shows a position of the locking spheres 68A, 68B. The locking spheres 68A, 68B provide a means for securement of the sickle blade 18 and the scaler blade 17 to the intraoral tool 16.

The spheres 68A, 68B are maintained by a tension spring 72 in a channel 72a that is provided in the protrusion 70. The tension spring 72 urges the locking spheres 68A, 68B within the channel 72a in an inward or outward direction, as shown by arrow 71. The locking spheres 68A, 68B bear against a pair of tapered openings 72b at opposite ends in the channel 72a that retain position of the locking spheres 68A, 68B in the channel 72a when the sickle blade 18 (or scaler blade 17) is not attached to the intraoral tool 16.

Referring to FIG. 16B, a cross-sectional view taken along line 16B-16B in FIG. 15, shows a receiver 74 portion integrated into an interior of the intraoral tool 16. The receiver 74 accepts the protrusion 70 of the sickle blade 18 or the scaler blade 17 when inserted into the intraoral tool 16. The blades 17, 18 are then urged in a direction shown by arrow 73 (see FIG. 16A) to lock the blades 17, 18 into engagement with the intraoral tool 16.

During insertion of the protrusion 70 into the receiver 74, in the direction of arrow 73, the locking spheres 68A, 68B retract into the channel 72a and permit the protrusion 70 to enter the receiver 74. The tension spring 72 allows the locking spheres 68A, 68B to retract into the channel 72a to allow complete insertion of the protrusion 70 of the sickle blade 18 (or scaler blade 17) into the receiver 74. When the insertion of the protrusion 70 is completely seated within the receiver 74, the tension spring 72 urges the locking spheres 68A, 68B outward, as shown by arrow 71, which secures the sickle blade 18 or the scaler blade 17 in position on the intraoral tool 16.

Referring back to FIG. 16A, removal of the sickle blade 18 (or scaler blade 17) is accomplished by applying a sufficient force to the sickle blade 18, or the scaler blade 17 in the direction of arrow 75 and simultaneously applying a force to the intraoral tool 16 in the direction of arrow 73. The opposing forces applied to the intraoral tool 16 and the sickle blade 18 (or scaler blade 17) cause the locking spheres 68A, 68B to retract inward 71 into the channel 72a allowing separation of the sickle blade 18 (or scaler blade 17) from the intraoral tool 16 to occur.

The component parts that have been selected for inclusion with the dental maintenance kit for animals 10 compliment each other in the performance of a comprehensive teeth cleaning or routine dental maintenance for the animal. This lessens the need for veterinarian appointments for animal teeth cleaning. The guide 14 provides instructions for the safe and effective use of the sickle blade 18 and scaler blade 17 in addition to instructions for the use of the other component parts included in the dental maintenance kit for animals 10.

A pet owner may elect to begin with plaque removal on the animal's teeth. The basic (i.e., standard or minimum) intraoral tool 16 configuration is to attach the sickle blade 18 and scaler blade 17 on each opposite end of the intraoral tool 16. This allows the user to perform a wide range of cleaning procedures to the animal's teeth. The scaler blade 17 is intended to be used in concert with the sickle blade 18 as part of a plaque and/or stain removal process.

The variety of components and parts included in the dental maintenance kit for animals 10 allows the pet owner to perform a basic cleaning between meals by removal of debris and plaque or a more comprehensive cleaning that includes use of the toothbrush 24.

An unexpected benefit from the invention is a safety release feature incorporated into the design of the locking mechanism (illustrated in FIG. 16A and FIG. 16B) provided by the locking spheres 68A, 68B. When excess force is applied to the intraoral tool 16 in the direction of arrow 73 in FIG. 16A such as when prying embedded debris from a groove of a tooth, the sickle blade 18 or the scaler blade 17 will detach from the intraoral tool 16 to prevent damage to the animal's teeth or other injury from occurring. This is a significant benefit unavailable with prior dental cleaning instruments.

An additional unexpected benefit is provided by the careful selection of the tension spring 72. A stronger spring constant for the tension spring 72 provides a higher release force to separate the scaler and the sickle blades 17, 18 from the intraoral tool 16 as compared to the use of a modified type of the tension spring 72 with a weaker spring constant. Selection of the spring constant for the tension spring 72 allows for different release points (i.e., different forces to cause separation to occur). For larger dogs, for example, a stronger release point (i.e., a greater force) is desired. For smaller dogs or for cats, for example, a lower release point (i.e., a lesser force) is desired. Accordingly, the dental maintenance kit for animals 10 can be offered in different versions that are ideally suited for each type of animal.

Another unexpected benefit from the invention is the potential for an overall reduction of expenses related to dental cleanings provided by a veterinarian that would need to be scheduled to maintain the animal's dental health.

In addition, the intraoral tool 16 provides another unexpected benefit. By placing the sickle blade 18 and the scaler blade 17 on each opposite end of the intraoral tool 16, a new configuration is provided that is especially useful for an unskilled person, such as a pet owner to use.

This is because a dental hygienist will normally use tools that have a scaler blade 17 at opposite ends or a sickle blade 18 at opposite ends. That way, the speed of cleaning is increased as the experienced professional dental hygienist alternately uses opposite ends of the same tool for the same type of cleaning on the upper and lower teeth or on the lingual and exterior sides of the teeth. By providing the intraoral tool 16 that includes both the sickle blade 18 and the scaler blade 17 simultaneously on the one tool (i.e., on the intraoral tool 16), the pet owner can with one tool clean all of the animal's tooth surfaces and all of the inter proximal areas (both lingual and exterior).

The intraoral tool 16 can, as desired, be configured by the user so that a variety of different combinations of the sickle blade 18 and scaler blade 17 can be attached to the intraoral tool 16 to provide maximum versatility in the use of the intraoral tool 16.

A dental prophylaxis tool that includes plastic for a handle (i.e., for the intraoral tool 16) and stainless steel for the blades 18, 17 is believed to be new. Dental tools that are currently available (i.e., prior art dental hygiene tools) are made entirely from stainless steel. By eliminating the use of steel for the body of the intraoral tool 16, a significant amount of steel is eliminated. This not only reduces cost but it also reduces the signature of the dental maintenance kit for animals 10 when passing through an airport security station. Accordingly, the dental maintenance kit for animals 10 does not appear as if it is a weapon and so it is not likely to become an issue should the dental maintenance kit be taken with the pet owner for use on the animal during travel or vacations.

The removable blades 17, 18 of the intraoral tool 16 allow for quick and easy replacement by the user. This helps permit more rapid dental cleaning.

A dental tool with the sickle blade 18 and the scaler blade 17 that includes a plastic coating which exposes only the working surfaces 63 of the sickle blade 18 or the scaler blade 17 also believed to be new. Known intraoral tools with a sickle blade 18 or a scaler blade 17 do not include a plastic safety coating 64 that is applied to the blade shaft or base. Some intraoral tools may include a plastic safety cap in the form of a small diameter tube placed over the working surface of the blade. This aforementioned safety cap must be removed prior to tool use and does not provide protection to gums and surrounding tissue during the cleaning process. This is especially important as it helps prevent an unskilled pet owner (person) from inadvertently cutting the animal's gums while cleaning the animal's teeth.

Intraoral tools with accompanying printed instructions for use of the tools by the unskilled person are also believed to be new. Current intraoral tools are packaged with the assumption that purchase will be by a qualified dentist or oral hygienist who would not require printed instructions.

If desired, other component parts may also be included in the dental maintenance kit for animals 10. For example, a tongue scraper (not shown) and/or a cheek retractor (not shown) could also be included in the dental maintenance kit for animals 10.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:
1. A dental maintenance kit for animals, comprising:
   (a) a storage container;
   (b) an intraoral tool, wherein said intraoral tool includes a handle having a longitudinal length and a pair of opposite ends, and wherein each of said opposite ends includes means for detachably-attaching a sickle blade or a scaler blade to each of said opposite ends, and wherein said handle is formed of a non-metallic material;
   (c) at least one sickle blade and at least one scaler blade that each include corresponding attachment means for cooperating with said means for detachably-attaching said at least one sickle blade or said at least one scaler blade;
   (d) and wherein said means for detachably-attaching said sickle blade or said scaler blade to each of said opposite ends includes a safety release that permits detachment of said sickle blade or said scaler blade apart from said intraoral tool in the event that an excessive force is applied to said intraoral tool that is urging said intraoral tool in a direction that is away from said sickle blade or away from said scaler blade;
   (e) wherein said storage container is able to contain said intraoral tool and said at least one sickle blade and said at least one scaler blade; and
   (f) wherein each of said sickle blades and each of said scaler blades includes a recessed area attached to said sickle blade and to said scaler blade proximate an active area of said sickle blade and said scaler blade, and wherein said recessed area is able to retain a quantity of toothpaste or animal food, therein.

2. The dental maintenance kit for animals of claim 1 wherein said means for detachably-attaching said sickle blade or said scaler blade to each of said opposite ends includes providing a recess in each of said opposite ends of said intraoral tool.

3. The dental maintenance kit for animals of claim 2 wherein said recess includes a generally square or rectangular cross-sectional shape and a predetermined depth into each of said opposite ends, and wherein said recess includes an indentation that is provided along at least one of four sides of said recess.

4. The dental maintenance kit for animals of claim 2 wherein said corresponding attachment means of said scaler blade and said sickle blade include a protrusion that is attached to a non-working end of said sickle blade and said scaler blade, and wherein said protrusion is able to be urged inside of said recess of said intraoral tool.

5. The dental maintenance kit for animals of claim 3 wherein said corresponding attachment means of said scaler blade and said sickle blade include a protrusion that has a generally square or rectangular cross-sectional shape and which is attached to a non-working end of said sickle blade and said scaler blade, and wherein said protrusion is able to be urged inside of said recess of said intraoral tool, and wherein said protrusion includes at least one locking sphere, and wherein a force is applied to said at least one locking sphere that urges a portion of said at least one locking sphere beyond a planar surface of said protrusion, and wherein said at least one locking sphere is able to be urged into said protrusion an amount sufficient to permit insertion of said protrusion into said recess, and wherein when said protrusion is fully inserted into said recess, said portion of said at least one locking sphere is urged beyond said planar surface of said protrusion an amount sufficient for said portion of said at least one locking sphere to enter into said indentation an amount sufficient to secure said protrusion in said recess.

6. The dental maintenance kit for animals of claim 5 wherein when said scaler blade or said sickle blade is attached to said intraoral tool and a sufficient force is applied to said intraoral tool in a first direction that is away from said scaler blade or said sickle blade and a sufficient force is applied to said scaler blade or said sickle blade in an opposite second direction, said at least one locking sphere is able to be urged into said protrusion an amount sufficient to permit release of said scaler blade or said sickle blade from either of said opposite ends of said intraoral tool.

7. The dental maintenance kit for animals of claim 1 including an instruction guide that provides instructions sufficient to permit an unskilled user to safely use said intraoral tool and said sickle blade or said scaler blade when attached to said intraoral tool.

8. The dental maintenance kit for animals of claim 1 including a toothbrush.

9. The dental maintenance kit for animals of claim 1 including a meat-flavored toothpaste, and wherein during use of said dental maintenance kit for animals, a quantity of said meat-flavored toothpaste is applied to said recessed area prior to placing said active area in a mouth of an animal.

10. The dental maintenance kit for animals of claim 1 including a container, wherein said container is able to contain a quantity of a meat-flavored toothpaste.

11. The dental maintenance kit for animals of claim 1 including a dental mirror.

12. The dental maintenance kit for animals of claim 1 including at least one replacement sickle blade or at least one replacement scaler blade.

13. An improvement to a sickle blade or to a scaler blade for use with an intraoral tool, wherein the sickle blade or the scaler blade is detachably-attachable with respect to the intraoral tool, wherein the improvement comprises a recessed area attached to the sickle blade and to the scaler blade proximate an active area of the sickle blade and the scaler blade, and wherein the recessed area is able to retain a quantity of toothpaste or animal food, therein, and including means for detaching the sickle blade or the scaler blade from the intraoral tool when a sufficient force is applied to the sickle blade or to the scaler blade urging the sickle blade or the scaler blade away from the intraoral tool.

* * * * *